United States Patent [19]

Suzuki et al.

[11] Patent Number: 5,281,415

[45] Date of Patent: Jan. 25, 1994

[54] SUSTAINED RELEASE COMPOSITION FOR APPLICATION TO THE ORAL CAVITY

[75] Inventors: Soji Suzuki; Tsutomu Harada, both of Kawasaki, Japan

[73] Assignee: Ajinomoto Co., Inc., Tokyo, Japan

[21] Appl. No.: 831,810

[22] Filed: Feb. 6, 1992

[30] Foreign Application Priority Data

Feb. 7, 1991 [JP] Japan ................. 3-102202

[51] Int. Cl.$^5$ ................ A61K 7/16; A61K 31/715
[52] U.S. Cl. .............. 424/78.37; 424/48; 424/49; 424/435; 424/439; 424/464; 426/658; 514/54
[58] Field of Search ............ 424/49, 48, 435, 464, 424/439

[56] References Cited

U.S. PATENT DOCUMENTS

| | | | |
|---|---|---|---|
| 4,285,735 | 8/1981 | Mitchell et al. | 536/128 |
| 4,863,719 | 9/1989 | Mays et al. | 424/49 |
| 4,915,948 | 4/1990 | Gallopo et al. | 424/435 |
| 5,098,730 | 3/1992 | Pepper et al. | 426/660 |

FOREIGN PATENT DOCUMENTS

| | | |
|---|---|---|
| 0055109 | 6/1982 | European Pat. Off. |
| 0059535 | 9/1982 | European Pat. Off. |
| 0377278 | 7/1990 | European Pat. Off. |
| 0102202 | 2/1991 | Japan ............... A23K 3/00 |

OTHER PUBLICATIONS

Abstract No. 86-260823/40 (one page). Aug. 21, 1986.

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

There is provided a novel composition for oral cavity application to which a sustained release property is imparted so as to effectively exhibit the effects of a component for preventing bad odor from the oral cavity and/or a flavor component and/or an anti-dental caries component in the oral cavity. By incorporating a β-2,1 linked fructose polymer as a polysaccharide together with a sweetener component, a component for preventing bad odor from the oral cavity and/or a flavor component and/or an anti-dental caries component, the residence time of the effective components described above can be prolonged in the oral cavity to enhance their effects and the residence time can also be controlled. That is, the composition for oral cavity application is characterized by sustained release of the effective components described.

4 Claims, No Drawings

SUSTAINED RELEASE COMPOSITION FOR APPLICATION TO THE ORAL CAVITY

CROSS-REFERENCE TO RELATED APPLICATION

This subject matter of this application is related to the subject matter disclosed in Ser. No. 07/753,446, filed Aug. 30, 1991 now U.S. Pat. No. 5,169,671.

TECHNICAL FIELD

The present invention relates to a composition for application to the oral cavity comprising a β-2,1 linked fructose polymer together with a sweetener component, a component for preventing bad odor from the oral cavity and/or a flavor component and/or an anti-dental caries component.

BACKGROUND OF THE INVENTION

Prior art compositions that have been used for application to the oral cavity generally comprise a component for preventing bad odor and/or a flavor component and/or an anti-dental caries component, and use sugars like sucrose, glucose, sorbitol, etc. as bulking agents. At the same time, sweetness is imparted by the sugars mentioned above. Various sugars may be employed as bulking agents depending on end use, but all prior art sugars dissolve rapidly and are quickly swallowed. Thus, any additives contained in a sugar composition whose effects are exhibited only when retained for long periods of time in oral cavity are not kept in the mouth long enough to be effective, and the desired results are generally not observed.

SUMMARY OF THE INVENTION

An object of the present invention is to provide a novel composition applicable to the oral cavity which is not susceptible to the aforesaid defects exhibited in prior art oral cavity compositions and that prolongs the residence time in the oral cavity of effective components such as components for preventing bad odor and/or flavor components and/or anti-dental caries components so that their desired effects may be fully exhibited.

DETAILED DESCRIPTION OF THE INVENTION

In order to solve the above-mentioned problems the present inventors have undertaken extensive investigations based upon their hypothesis that if a polysaccharide having a sustained release property and having agreeability to the palate can be incorporated into a composition for oral cavity application such as a candy and a chewing gum, the residence time of the composition in the oral cavity can be prolonged and controlled. As a result, it has been found that the problems encountered with prior art compositions have been solved.

That is, it has been found that when a β-2,1 linked fructose polymer is incorporated as a bulking agent together with a sweetener component, a component for preventing bad odor from the oral cavity and/or a flavor component and/or an anti-dental caries component, the residence time of the effective component(s) in the oral cavity can be prolonged as compared to conventional compositions for oral cavity application. As a result, the effects of the active components in the composition can be enhanced and the residence time in the oral cavity can be controlled, that is, the release of these effective components can be sustained over long periods of time.

When practicing the present invention, if an anti-dental caries component is used it is preferrable not to use as sweetener sugars such as glucose, sucrose, etc. because they cause the dental caries. It is therefore preferred to use a mixture of a sweetener having a high degree of sweetness which does not cause dental caries, for example, α-L-aspartyl-L-phenylalanine methyl ester (hereafter simply referred to as asparteme), stebioside, glycyrrhizin, saccharine, Acesulfam K, etc. or a mixture thereof, etc., and β-2,1 linked fructose polymer as bulking agents. These sweetners can also be used in the absence of an anti-dental caries component.

Where a sweetener having a high degree of sweetness is used as the sweetener component, it is sufficient to add the sweetener generally in an amount corresponding to the same degree of sweetness as that of sugars such as sucrose to be replaced, or to add the bulking agent composition corresponding to the same sweetness degree as that of sugars such as sucrose to be replaced. Basically, the amount of the sweetener composition used is determined depending upon size of the composition for oral cavity application and the amount of sugar component, such as sucrose, used.

The components for preventing bad odor from the oral cavity which may be used in the present invention comprise one or more beefsteak plants such as rosemary or sage which have a deodorant effect on bad odor components like methylmercaptan, etc.; seaweeds selected from *Eisenia bicyclis, Hijikia fusiformis, Sargussum fulvellum, Chondrus ocellatus, Gracilaria confervoides, Nemacystus* and Undaria pinnatifida and mace which also exhibits the effect of preventing periodontal disease, etc., as well as extracts of these materials with solvents, purified products of these extracts and/or living organisms and/or dried products thereof. The amount of these materials used is in the range of 0.001 to 50 wt % based on the final product.

The flavor components which can be used in the present invention can be any flavor which is conventionally used in compositions for oral cavity application such as a chewing gum and retained in the oral cavity to exhibit a favorable effect such as, for example, the flavor of citruses, coffee, tea, mint, herb, etc. The amount of these materials used is in the range of 0.001 to 50 wt. % based on final product.

The anti-dental caries component which can be used in the present invention includes dextranase or mutanase, which are enzymes for decomposing dental plaque. As the dextranase, there may be used dextranase obtained from known dextranase-producing bacteria belonging to the Ketosium sp., Penicillium sp., Aspergillus sp., Spicaria sp., Lactobacillus sp., Ceilubivrio sp., etc. by known methods. This enzyme decomposes β-1,6-glucan which is a kind of dental plaque and is incorporated generally in an amount of 100 to 100,000 units per gm. of the product, when calculated as enzyme.

As the mutanase, there may be used mutanase obtained from known mutanase-producing bacteria belonging to the Pseudomonas sp., Trichoderma sp., Cladosporium sp., Flavobacteri-um sp., Streptomyces sp., etc. by known methods. This enzyme decomposes α-1,3-glucan which is a kind of dental plaque and is incorporated generally in an amount of 50 to 10,000 units per gm. of the product, when calculated as enzyme.

The β-2,1 linked fructose polymer of the present invention refers to a fructose polymer having a β-2,1 type bond, for example, inulin, fructose polymer produced by *Aspergillus sydowi* as per Japan 61-187797, etc. or a mixture thereof. The β-2,1 fructose polymer is also described in copending U.S. Ser. No. 07/753,446, filed Aug. 30, 1991 incorporated herein by reference, and is sometimes described as a polyfructan. Its molecular weight distribution is in the range of 2,000 to 50,000,000, preferably 10,000 to 15,000,000. The amount added is in the range of 1 to 50 wt %, preferably 2 to 30%, based on the final product. With less than 1 wt %, a desirable effect is not exhibited.

Further, when the amount exceeds 50%, it is not that this amount of polymer may not be used, but one would generally feel a somewhat hard texture, though it depends on the individual preference of texture, that is, such an amount (>50% by wt.) gives an oral cavity composition which might have no agreeability to the palate of consumers. In preparing these oral cavity compositions, the fructose polymer may be used in a powdery form or may be suspended in water, etc. and the suspension and/or solution in water may be used. The form of the fructose polymer may be chosen depending upon its preparation.

The present inventors have studied the residence time in the oral cavity of polysaccharides and their ability to impart sustained release using a variety of polysaccharides including the fructose polymer described above and found that polydextrose, gums such as guar gum, and other polysaccharides such as starch perform quite poorly because these substances are very hygroscopic, are very slow in dispersing in water, are extremely high in viscosity, are insoluble in water, are gelatinized, or impart an undesirable taste with astrigency, and different flavor, etc.

However, the β-2,1 linked fructose polymer used in the present invention has a low hygroscopic property, provides an extremely low viscosity when dispersed in water, is gradually dispersed but free of marked swelling when dispersed, does not impart an undesired taste and flavor, shows no paste-like texture or feel inherent to the above other polysaccharides and gives an extremely smooth dispersion as compared to the aforesaid polysaccharides. That is, the physical properties and textural qualities of a composition using the β-2,1 linked fructose polymer are equal to or superior to conventional products using sugars.

Surprisingly, it has also been discovered that when the fructose polymer having the above-mentioned properties is incorporated into an oral cavity composition, for example, a candy, malt syrup, a cake tablet, a troche, etc., it is possible to control the oral solubility of the products, especially dissolution velocity, by increasing or decreasing the amount of the fructose polymer added. That is, the residence time of the oral cavity composition can be controlled to a desired time period depending upon the amount of the added fructose polymer. Furthermore, it is not observed that the readily orally soluble component in the oral cavity composition comprising the fructose polymer selectively dissolves out. Therefore, the component for preventing bad odor from the oral cavity and/or flavor component and/or anti-dental caries component in accordance with the present invention can be retained in the oral cavity for a time sufficient for it to exhibit its function satisfactorily, which was impossible in prior art compositions. That is, the effective components can be retained in the oral cavity in such a state that the components are imparted through sustained release.

Therefore, the oral cavity composition using the aforesaid β-2,1 linked fructose polymer does not adversely affect the quality, namely, the physical properties such as hygroscopic property, etc. and organoleptic preferences of the oral cavity composition and provides oral cavity compositions such as a candy, malt syrup, a cake tablet, a troche, etc. with qualities which are not provided by the prior art. The oral cavity composition is not limited to those shown above, and is also applicable to a chewing gum, a throat troche, a drop, a tooth paste, gargle for deodorization, a drug for stomatitis, etc.

Thus, according to the present invention, there is provided an oral cavity composition, for example, a candy, malt syrup, a cake tablet, a troche, etc., which is characterized by containing a β-2,1 linked fructose polymer together with a sweetener component, a component for preventing bad odor from the oral cavity and/or a flavor component and/or an anti-dental caries component, whereby the effects of these additive components is enhanced.

Next, the present invention is specifically described by referring to the Examples below. The Examples are given solely for the purposes of illustration and are not to be construed as limitations of the present invention as many variations of the invention are possible without departing from its spirit and scope.

EXAMPLES

Example 1

A cake tablet having a coffee flavor was prepared according to the following formulation: (all %'s are % by wt.)

For control, glucose was used. In Test groups, fructose polymer produced by *Aspergillus sydowi* was used in amounts of 50% (Test Group 1) and 25% (Test Group 2), in place of glucose.

| Control Group: | Glucose | 92.7% |
|---|---|---|
| | Aspartame | 0.6 |
| | Instant coffee powder | 0.6 |
| | Coffee flavor | 0.2 |
| | Sodium aspartate | 0.06 |

The raw materials were blended, kneaded and then sieved through a sieve of 50 mesh followed by molding 2.0 g at 60 atoms for 2 minutes. Test Group 1 was made with the ingredients of the Control Group using 46.4% of glucose and 46.3% of the fructose polymer In the cases of 25% substitution (Test Group 2), 69.5% of glucose and 23.2% fructose polymer were used.

Example 2

The solubility of the Control Group, Test Group 1 and Test Group 2 prepared above was examined in terms of their dissolution velocity in distilled water at 40° C. (a model of the oral cavity).
Control Group: 1.5 minutes
Test Group 1: 150 minutes
Test Group 2: 12.5 minutes From the foregoing results, the residence time of the test groups in the oral cavity is prolonged more than 10 times over that of the Control Group. In addition, the solubility control obtained by changing the amount of the fructose polymer formulated in the composition is demonstrated with concomitant gradual release of the coffee flavor.

Example 3

In addition to Control Group, Test Group 1 and Test Group 2 prepared by way of experiment above, Test Group 3 was prepared as above with polydextrose substituted for 50% of glucose. With respect to the four groups in total, hygroscopic properties under a relative humidity of 58% was examined in terms of % weight increase due to adsorption of humidity and any change in appearance.

Control Group: hygroscopic rate (% increase in weight) 0.5%; no change in appearance Test Group 1: hygroscopic rate 1.9%; no change in appearance Test Group 2: hygroscopic rate 1.2%; no change in appearance Test Group 3: hygroscopic rate 4.9%; deliquescent on the surface From the foregoing results, it is shown that there is no difference in hygroscopic property between the test groups using the $\beta$-2,1 linked fructose polymer and the control group using glucose.

Example 4

Next, Test Group 1 and Test Group 2 were subjected to organoleptic evaluation (panel persons: 10) and compared to the Control Group. The evaluation was made in terms of (1) dissolution time in the oral cavity, (2) quality of taste and (3) preference as evaluated by the number of persons who chose a particular sample as the best one.

Test Group 1: (1) 10 minutes; (2) no difference from the control group; (3) preference: 6

Test Group 2: (1) 6.5 minutes; (2) no difference from the control group; (3) preference: 8

Control Group: (1) 3.5 minutes; (2) -; (3) preference: 5

As shown by the data above, where the $\beta$-2,1 linked fructose polymer was used, a table cake having a coffee flavor with sustained release of effective components could be prepared with the same or better organoleptic and sensory qualities as those using sugars.

What is claimed as new and desired to be secured by Letter Patent of the United States is:

1. A composition for application to the oral cavity comprising 1–50 wt. % of a $\beta$-2,1 linked fructose polymer together with at least one sweetener component and at least one of a component for preventing bad odor from the oral cavity, a flavor component and an antidental caries component.

2. A composition for application to the oral cavity as claimed in claim 1, wherein said sweetener component comprises at least one of $\alpha$-L-aspartyl-L-phenylalanine methyl ester, stebioside, glycyrrhizin, saccharine and Acesulfam K.

3. A composition for application to the oral cavity as claimed in claim 2, wherein $\alpha$-L-aspartyl-L-phenylalanine methyl ester is the sweetener having a high degree of sweetness.

4. A composition for application to the oral cavity as claimed in claim 1, wherein the molecular weight of the $\beta$-2,1 linked fructose polymer is in the range of 2,000 to 50,000,000.

* * * * *